Oct. 24, 1967 E. S. BOERNER Plant Pat. 2,774
ROSE PLANT
Filed Sept. 1, 1966
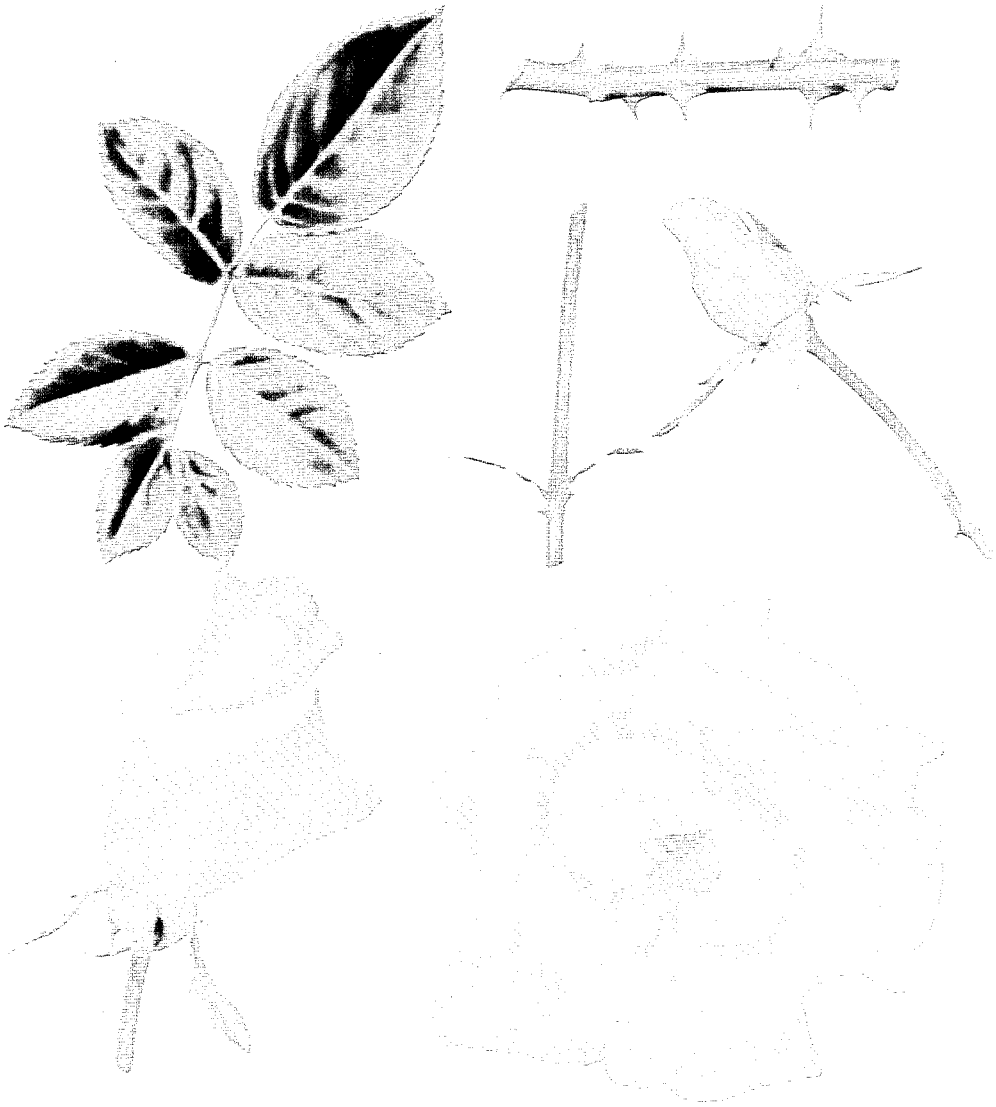
Inventor.
E. S. Boerner
By: Robb & Robb
Attorneys.

United States Patent Office

Plant Pat. 2,774
Patented Oct. 24, 1967

2,774
ROSE PLANT

Eugene S. Boerner, Newark, N.Y., assignor to Jackson & Perkins Company, Newark, N.Y., a corporation of New York Filed Sept. 1, 1966, Ser. No. 577,106
1 Claim. (Cl. Plt.—11)

The present invention relates to a new and distinct variety of rose plant of the hybrid tea class, which was originated by me by crossing an unnamed and unpatented giant seedling of the variety known as "Golden Masterpiece" (Plant Patent No. 1,284) with an unnamed and unpatented seedling of the variety known as "Enchantment" (Plant Patent No. 737).

The primary objective of this breeding was to produce a new rose variety which bears flowers combining a large size and a distinctive Rose Red color. This objective was fully achieved, along with other desirable features, as evidenced by the following unique combination of characteristics which are outstanding therein and which distinguish it from its parents, as well as from all other varieties of which I am aware:

(1) A vigorous and upright habit of growth;
(2) Abundant foliage;
(3) Large flower size; and
(4) A distinctive and attractive general color tonality of the flowers corresponding to Rose Red, lightly overcast with Begonia Rose.

Asexual reproduction of my new variety by budding, as performed at Newark, N.Y., and also at Pleasanton, Calif., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—An unnamed giant seedling of "Golden Masterpiece."
*Pollen parent.*—An unnamed seedling of "Enchantment."

Classification:
*Botanic.*—Hybrid tea.
*Commercial.*—Hybrid tea.

*Flower*

(Observations made from specimens grown outdoors at Newark, N.Y., in the early morning during the latter part of the month of June.)

Blooming habit: Recurrent—continuous.

Bud:
*Size.*—Large.
*Form.*—Ovoid; is not affected by wet or hot weather.
*Color.*—When sepals first divide—Carmine, Plate 1. When petals begin to unfurl—Carmine, Plate 1, very lightly overcast with Scarlet-Red, Plate 1. When half-blown: inside of petals—Begonia Rose, Plate 1, very lightly overcast in the center of the petal with Hermosa Pink, Plate 1; reverse of petals—Rose Red, Plate 12, very lightly overcast with Scarlet-Red, Plate 1.
*Sepals.*—Smooth edge; branched; curl back when petals begin to unfurl. Color: inside—Grape Green, Plate 41; outside—Light Hellebore Green, Plate 17.

*Calyx.*—Color—light Cress Green, Plate 31. Shape—funnel. Size—long. Aspect—smooth. Odor when rubbed—none.
*Peduncle.* — Length — medium. Aspect — smooth. Strength—erect; heavy. Color—buffy Citrine, Plate 16.
*Opening.*—Opens up well; is not affected by adverse weather conditions.

Bloom:
*Size.*—Large. Average size when fully expanded—from 5 inches to 5½ inches.
*Borne.*—Both singly and several together.
*Stems.*—Long; strong.
*Form (when first open).*—Cupped. Permanence—retains its form to the end; outer petals turn back.
*Petalage.*—Double (full but open center). Number of petals under normal conditions—from 25 to 30.
*Color.*—Center of flower—Rose Red, Plate 12, lightly overcast with Begonia Rose, Plate 1. Outer petals—Rose Red, Plate 12, very lightly overcast with Spinel Pink, Plate 26. Base of petals (aiglet)—Primrose Yellow, Plate 30. Inside of petals—Eosine Pink, Plate 1, very lightly overcast with Thulite Pink, Plate 26 with the lower half of petal very lightly overcast with Spinel Pink, Plate 26. Reverse of petals—Rose Red, Plate 12, very lightly overcast with Scarlet-Red, Plate 1. General tonality from a distance—Rose Red, Plate 12, lightly overcast with Spinel Pink, Plate 26.
*Discoloration.*—General tonality at end of first day—Rose Red, Plate 12, lightly overcast with Begonia Rose, Plate 1. Second day—Rose Red, Plate 12, lightly overcast with Begonia Rose, Plate 1. Third day—Rose Red, Plate 12, lightly overcast with Spinel Pink, Plate 26.

Petals:
*Texture.*—Leathery; is not affected by wet or hot weather.
*Appearance.*—Inside—shiny. Outside—satiny.
*Form.*—Oval; slightly notched.
*Arrangement.* — Imbricated (regularly arranged shingle-like).
*Petaloids in center.*—Few; small.
*Persistence.*—Drop off cleanly.
*Fragrance.*—Moderate. Nature—tea (average hybrid tea scent).
*Lasting quality.*—On the plant—long. As cut flower—long.

*Genital organs*

Stamens, anthers: Large; many; regularly arranged around styles. Color—Capucine Orange, Plate 3.
Stamens, filaments (threads): Medium length. Color—Light Buff, Plate 3.
Pollen: Color—Capucine Buff, Plate 3.
Styles: Bunched; uneven length; medium length; thin.
Stigmas: Color—Cream Buff, Plate 30.
Ovaries: All enclosed in calyx.
Hips: None.
Seeds: None.

*Plant*

Form: Bush.
Growth: Vigorous; upright.
Foliage: Compound of 5 to 7 leaflets.
*Size.*—Large.
*Quantity.*—Abundant.
*Color.*—New foliage: upper side—Biscay Green, Plate 17; under side—Yellowish Citrine, Plate 16. Old foliage: upper side—Forest Green, Plate 17; under side—Courge Green, Plate 17.
*Shape.*—Oval pointed.

*Texture.* — Upper side — leathery. Under side — smooth.

*Ribs and veins.*—Ordinary.

*Edge.*—Serrated (saw toothed).

*Serration.*—Both double and single; small.

*Leaf stem.*—Color—Lettuce Green, Plate 5. Under side—rough.

*Stipules.*—Medium length; smooth.

Wood:

*New wood.*—Color—Oil Green, Plate 5. Bark—smooth.

*Old wood.*—Color—Grass Green, Plate 6. Bark—smooth.

Thorns:

*Thorns.*—Quantity: on main stalks from base—ordinary; on laterals from stalk—ordinary. Form—flat base; medium length; some hooked downward and some hooked upward. Color (when young)—Tawny, Plate 15. Position—irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novelty by the unique combination of a vigorous and upright habit of growth, abundant foliage, large flower size, and a distinctive and attractive general color tonality of the flowers corresponding to Rose Red, lightly overcast with Begonia Rose.

No references cited.

ABRAHAM G. STONE, *Primary Examiner.*

ROBERT E. BAGWILL, *Examiner.*